United States Patent [19]
Davankov

[11] Patent Number: 5,545,131
[45] Date of Patent: Aug. 13, 1996

[54] ARTIFICIAL KIDNEY

[75] Inventor: Vadim A. Davankov, Moscow, Russian Federation

[73] Assignee: White Eagle International Technologies, LP, New York, N.Y.

[21] Appl. No.: 346,871

[22] Filed: Nov. 30, 1994

[30]     Foreign Application Priority Data

Apr. 28, 1994  [RU]   Russian Federation ............... 4013703

[51] Int. Cl.$^6$ .................................................. A61M 37/00
[52] U.S. Cl. ................................................. 604/5; 210/646
[58] Field of Search ............. 604/4, 6, 29; 210/646–648

[56]                References Cited

U.S. PATENT DOCUMENTS 3,483,867  12/1969  Markovitz .
4,183,811  1/1980   Walch et al. .
4,312,757  1/1982   Brumfield .

Primary Examiner—Robert A. H. Clarke
Attorney, Agent, or Firm—Ilya Zborovsky

[57]                ABSTRACT

An artificial kidney system comprises an artificial kidney forming container having an inlet blood port connectable with a patient's artery and an outlet blood port connectable with a patient's vein so that blood from the patient's artery can flow through the inlet port into the container, then through an inner space of the container and then through the outlet blood port into the patient's vein, the inner space of the container being filled with an adsorbent for removing harmful and toxic compounds from a stream of blood flowing in the inner space from the inlet blood port to the outlet blood port, the container being provided with a separate chamber formed inside the inner space and limited by a semi-permeable polymeric ultrafiltration-type membrane which allows water and dissolved small molecules to be transported from blood into the chamber, and suction element connectable with the separate chamber so that the water and the dissolved small molecules are transported from blood into the separate chamber and further outside of the container under the action of suction of the suction element.

14 Claims, 2 Drawing Sheets

ARTIFICIAL KIDNEY

BACKGROUND OF THE INVENTION

The present invention relates to an artificial kidney.

It is known that kidneys of living organisms are important excretory organs whose main functions are to remove both the superfluous water and the biologically useless as well as toxic materials accumulating in the blood. The human kidney is composed of 1–1.5 million microscopic subunits called nephrons. Each nephron in turn has a complex structure with two main parts: the glomerulas and the tubules. In the glomerulas the blood plasma is filtrated from blood capillary vessels through porous walls of these vessels. The filtrate drains into the tube system forming the tubules where the major part of water and plasma components are readsorbed into the efferent blood vessels. The remaining liquid containing all biologically useless materials in a high concentration is the urine that passes through the ureter to the urinary bladder. Approximately 180 liters per day of blood passes through the kidneys producing only approximately 1.5 liters of urine.

Urine contains hundreds of organic compounds, most important of them being the protein digestion and metabolism products, urea, creatinine, uric acid and some others. When kidneys cannot operate properly, useless and/or toxic materials accumulate in blood and other physiological fluids and lead to death within 10–12 days. Replacing the ill kidney with a healthy one by transplantation stimulates the rejection mechanisms of the living body against the foreign organ, unless the donor is a close relative. Therefore, antirejection drugs must be given to the recipient patient, which always have some harmful side effects. Therefore, a transplanted kidney cannot generally be expected to keep functioning for more than five years.

The only alternative way of removing excess water and biologically useless low-molecular-weight organic compounds from the organism is external hemodialysis. By letting blood or blood plasma to equilibrate with a special dialysate aqueous solution through a semi-permeable polymeric membrane, this technique allows both the excess water and small molecules to migrate down the concentration gradient from the blood into the dialysate fluid. The pores of the membrane are usually chosen small enough in order to prevent larger molecules such as proteins from diffusion. For smaller molecules, the sole driving force for diffusion is the concentration gradient, since these molecules after having passes the membrane are constantly removed by a flow of fresh dialysate liquid. This mechanism holds for the water removal as well, since the dialysate fluid additionally contains salt in high concentrations, which diminishes the activity of water or which is basically the same, causes a difference in the osmotic pressures on the opposite sides of the membrane.

Hemodialysis is a slow process, which keeps the patient connected to the dialysis machine for several hours. This procedure has to be repeated three or four times a week. Besides the high consumption of the physiological dialysate fluid (about 120 liters), the technique is expensive as well as unpleasant and inconvenient for the patient. The patient will feel unwell both before and after dialysis. Before dialysis the waste products build up in the body, and after dialysis there is a dramatic distortion of the balance of chemical equilibria and processes in the body due to removal of the whole pool of molecules of the molecular weight of less than 500 dalton. Among these molecules are all amino acids, nucleotides, mineral ions and many other useful components. To minimize the loss of essential components during dialysis, the physiological dialysate fluid is doped with Na, K, Cl, Ca, Mg, acetate, bicarbonate and glucose. It would be too expensive, if possible at all, to add other components to the fluid. This drawback of the technique results from the unselectivity of the diffusion process through the polymeric membrane: the latter does not distinguish between useful and useless molecules. This unavoidable harmful effect would be expressed much less, if the removal of small molecules would be slow and constant instead of being made three or four times a week with a total clearance.

Two U.S. Pat. Nos. 5,092,886 and 4,769,037 disclose implantable artificial kidneys which should mimic the processes of filtration and partial readsorption of useful components that are characteristic for the living kidneys. The first patent suggests an extremely complicated system of tubes embedded in one another with the inner tubes having permeable porous walls and the outer tubes having impermeable walls. After arriving at a certain cross-over point, the outer impermeable tube should enter the interior of the previously inner permeable tube, with the permeability of the walls of the tubes inverting. This should provide the possibility for the reversal of filtration, i.e. give rise to readsorption of useful components.

The physico-chemical feasibility of these procedures raises serious doubts. Contrary to permeation through a biological membrane, which is an active specific transportation of selected molecules, diffusion through the polymeric membrane is nothing more than a simple size-restricted down-gradient flow of molecules, which is totally unspecific with respect to biological value of the compound. Therefore, no selective removal of waste products and no selective readsorption of useful compounds can be organized by ultrafiltration, regardless of the fact that the diffusion proceeds from the inner tube into the outer one or vice versa. Small molecules always display the tendency of appearing at equal concentrations on both sides of a polymeric ultrafiltration membrane. The patented project does not even try to consider gradients of concentrations as a driving force for diffusion of compounds, neither pressure differences as the driving force for the overall flow of fluids from one chamber into another.

The same disadvantages are characteristic of the other U.S. Pat. No. 4,769,037 which suggests placing sponge-like polymeric materials between extremely complicated hollow panels made of semipermeable membranes.

SUMMARY OF THE INVENTION

Accordingly, it is an object of the present invention to provide an artificial kidney, which avoids the disadvantages of the prior art and provides for highly advantageous results.

More particularly, it is an object of the present invention to provide an artificial kidney, in accordance with which diffusion through a polymeric microporous membrane is primarily size-selective, selective removal of certain types of molecules from solutions can be achieved through adsorption technique, and a controlled flow of liquids through a membrane is achieved by a definite difference of pressures on two sides of the membrane.

Thus, the present invention deals with an extracorporeal portable artificial kidney system and a method of operating the same, which combine a selective adsorption of middle-sized and less-polar smaller size molecules on a polymeric adsorbent by hemoperfusion with a non-selective removal of polar small molecules and excess water from blood by a vacuum-operated ultrafiltration process.

In keeping with these objects and with others which will become apparent hereinafter, one feature of the present invention resides, briefly stated, in an artificial kidney forming container having an inlet blood port connectable with an artery, and outlet blood port connectable with a vein, and an outlet urine port for urine, said container having an inner chamber filled with an adsorbent for removing harmful and toxic components from a stream of blood flowing through said container from said inlet blood port to said outlet blood port, said container having a separate chamber located in said space and having a porous semi-permeable ultrafiltration-type wall which allows water and dissolved small molecules to be transported from blood to said urine outlet port; and an artificial urinary bladder forming vessel which contains vacuum and is connected with said outlet urine port of said artificial kidney forming container so that the water and the dissolved small molecules are transported from said separate chamber through said urine outlet port into said artificial urinary bladder forming vessel under the action of vacuum in the latter.

When the artificial kidney is designed in accordance with the present invention, it eliminates the disadvantages of the prior art and provides for the above mentioned highly advantageous results as will be explained hereinbelow.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF THE PREFERRED EMBODIMENTS

Figure 1A:
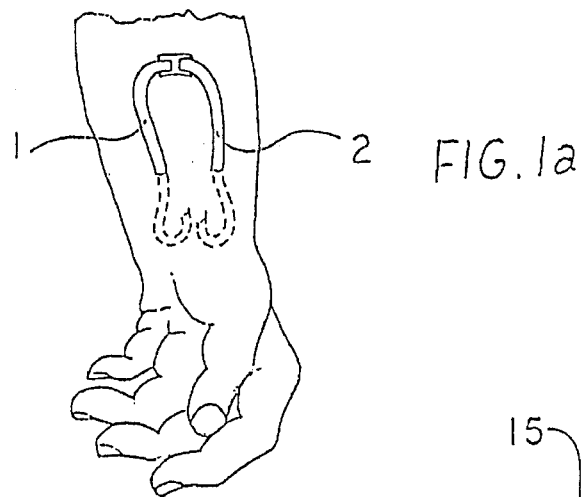
FIG. 1a of the drawings is a view showing elements of the artificial kidney in accordance with the present invention.
Figure 1B:
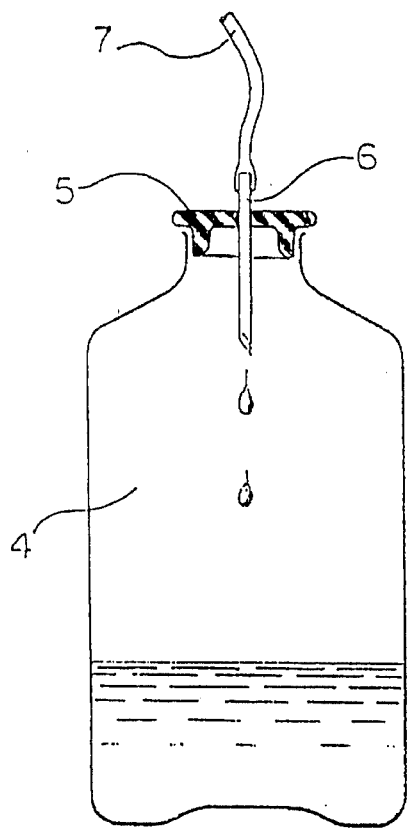
FIG. 1b of the drawings is a view showing elements of the artificial kidney in accordance with the present invention.
Figure 1C:
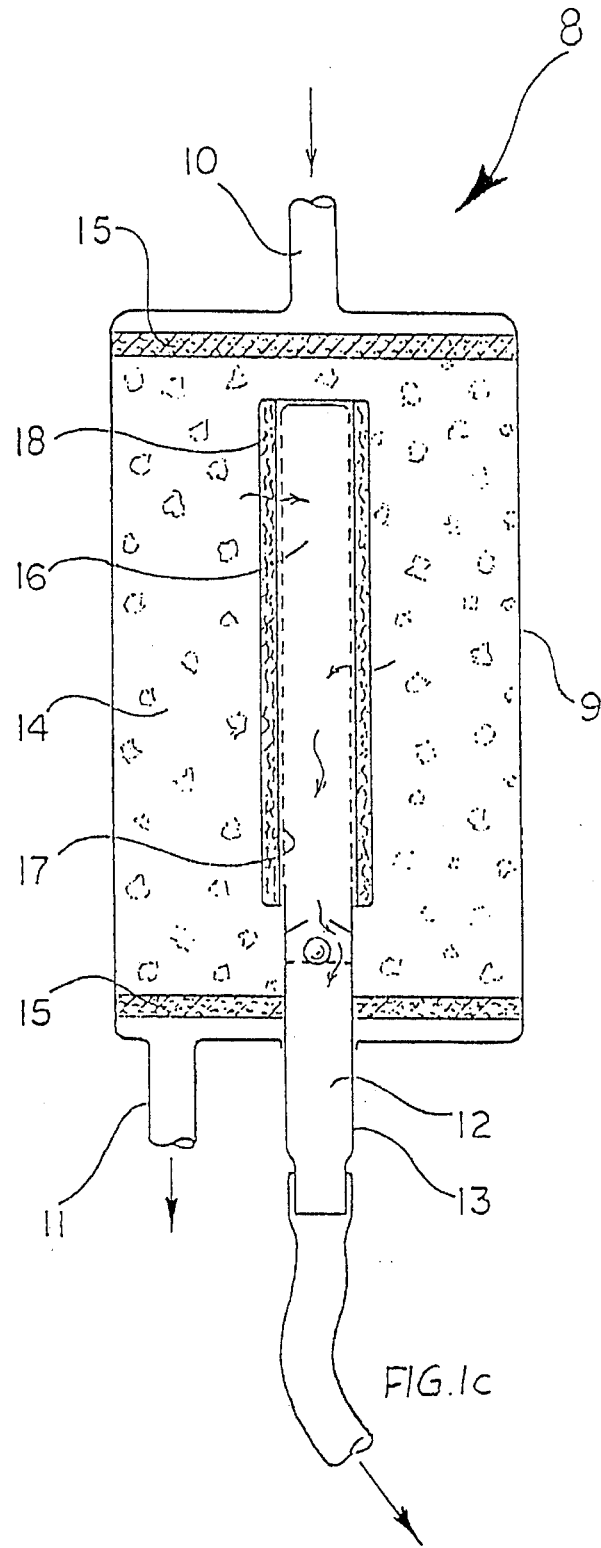
FIG. 1c of the drawings is a view showing elements of the artificial kidney in accordance with the present invention.
Figure 2:
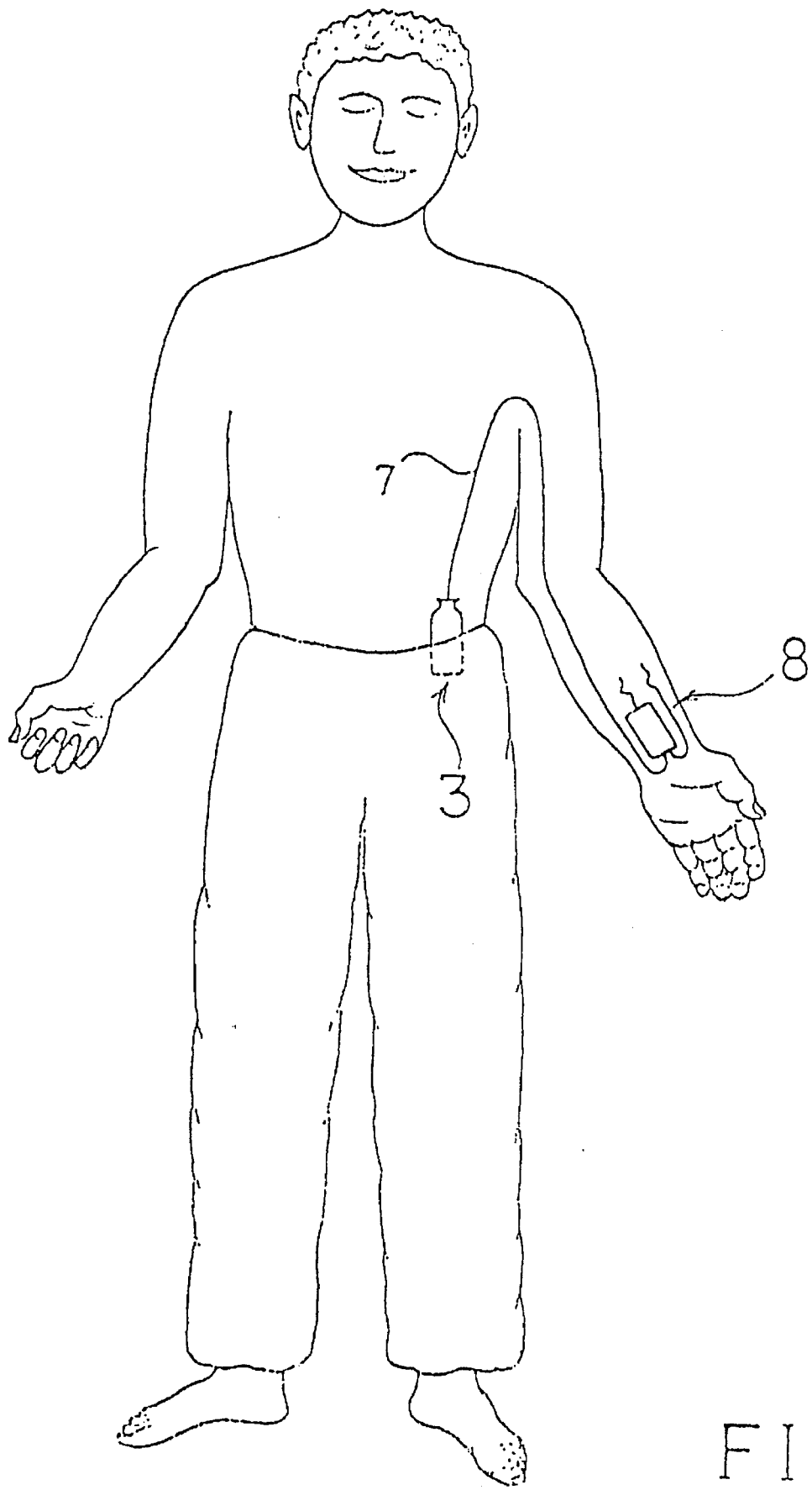
FIG. 2 is a view showing a patient provided with the artificial kidney in accordance with the present invention.

In a system which includes an artificial kidney in accordance with the present invention an arterial cannula which is identified with reference numeral 1 is implanted in a radial artery of a patient's wrist together with a venous cannula which is identified with reference numeral 2 implanted in the cerphalic vein adjacent to the radial artery, as well known in the art. Other appropriately situated artery and vein paths can be engaged as well. When the cannulas 1 and 2 are connected to each other, blood flows continuously through the tubes. When, however, the cannulas 1 and 2 are separated and connected to corresponding ports of the artificial kidney as will be explained hereinbelow, blood flows through the artificial kidney, and the blood flow is provided by a pressure difference in the artery and vein which is in the order of magnitude of 40 to 50 mercury mm.

The system is further provided with an artificial urinary bladder 3 which is formed as portable and replaceable glass, metal or plastic vessel 4 containing vacuum and closeable with a rubber seal 5. The vacuum can be produced in the vessel 4 by outside means; however, in a simple case when the vessel 4 is elastic, it can be squeezed so as to expel air from its interior and then relaxed so as to expand and form vacuum in it. A hollow metal needle pierces through the rubber seal 5 so that its one end extends into the interior of the vessel 4 and its another end is located outside the same.

An artificial ureter can be formed as a sufficiently long and thin rubber or plastic tube which has one end connected to the outside end of the hollow metal needle 6. Its opposite end is connected with an artificial kidney which will be explained in detail hereinbelow.

The artificial kidney is identified as a whole with reference numeral 8. It includes a closed container 9 provided with an inlet blood port 10 and an outlet blood port 11. The inlet blood port 10 is connected to the arterial cannula 1 while the outlet blood port 11 is connected with the venous cannula 2. The container 9 further has an outlet urine port 12 provided for discharge of urine and connected to the artificial ureter 7. The urine outlet port 12 has a check valve 13 which allows a filtrate to flow from the container 9 to the artificial ureter 7 under the action of vacuum in the vessel 4, but does not allow the liquid to move in the opposite direction. The container 9 of the artificial kidney is filled with an adsorbent 14 for removing harmful and toxic compounds from the stream of blood which flows from the inlet blood port 10 to the outlet blood port 11 passing along the adsorbent beads. Porous filters 15 are arranged at both sides of the container 9 between the ports 10 and 11 and the adsorbent 14. Inside the container 9 of the artificial kidney, a separate chamber 16 is formed. The chamber 16 can be limited by a wall 17 composed of a porous material and coated with a semi-permeable polymeric ultrafiltration-type membrane 18 which allows water and dissolved small molecules to be transported from blood into the chamber 15 and further through the ureter 7 into the vessel 4 of the artificial bladder 3 under the action of suction produced by the vacuum in the vessel 4.

The artificial kidney system in accordance with the present invention operates in the following manner:

The inlet blood port 10 and the outlet blood part 11 of the artificial kidney 8 are connected to the corresponding blood cannulas 1 and 2. The blood from the patient's artery flows from the inlet port 10 through the adsorbent bed 14 and, in accordance with the well known extracorporeal hemoperfusion procedure, the adsorbent removes certain kind of toxicants from the blood before the latter enters the patient's vein. When in addition to this, the hollow needle 6 of the artificial ureter 7 is inserted through the seal 5 into the vessel 4 of the artificial bladder 3, the ultrafiltration chamber 16 of the container 9 of the artificial kidney is exposed to vacuum and, in accordance with extracorporeal ultrafiltration process, water of the blood together with dissolved small molecules starts to filtrating through the membrane 17 into the chamber 16 and then through the valve 13 and the artificial ureter 7 flows into the vessel 4 of the artificial bladder 3 until the latter becomes filled with the filtrate. Then, the container 4 can be disconnected from the system at any time, in order to be replaced with a new container or in order to stop the ultrafiltration process. During the ultrafiltration process, the excess water together with the urea and some other small molecules is removed from the patient's body. This permanent process of ultrafiltration or the process which can be repeated several times per day washes out urea and other toxic compounds from the patient's body without causing a dramatic and sudden change in the concentration of all small molecules in blood, which is characteristic of the hemodialysis procedure.

Many kinds of biocompatible specific adsorbents, including affinity adsorbents, immuno adsorbents or immobilized enzymes can be provided in the container 9 of the artificial kidney 8, which could prove useful for some specific treatment of the patient. In more general case, however, a biocompatible non-specific adsorbent can be used selected from activated charcoal or polymeric adsorbent, in particular hypercrosslinked polystyrene-type adsorbent.

The blood cannulas 1, 2, the container 9 of the artificial kidney 8, and the ultrafiltration membrane 18 can be composed of or coated with any biocompatible polymeric material, including polytetrafluoroethylene, polyurethane, silicon rubber, carbine which is a linear modification of carbon, polyphosphasene, cellulose derivatives or others. The same is true for the filters 15.

The vacuum vessel 4 of the artificial urinary bladder 3 can be designed in many possible ways. Its functional role is collecting the filtrate and providing vacuum to the ultrafiltration chamber 16. The first function determines the size and shape of the vessel, having in mind the convenience of the patient who should carry the vessel for example in a special pocket of his dress. From this point of view, the preferred size of the container should be between 200 and 600 ml. For a replaceable container made of metal, glass or any hard polymer, a rubber seal 5 which can be pierced by the hollow metal needle 6 is the simplest but not the only possible way of connecting to the artificial ureter 7 with simultaneous transmission of vacuum to the ultrafiltration chamber 16.

An alternative to the replaceable vacuum vessel is a permanent container that can be emptied by squeezing with hands of the patient at any convenient moment. In this case, the vessel 4 can be made from an elastic polymer and it should be provided with two check valves one at the inlet of the container and the other at the outlet of the container. Vacuum is generated in the vessel due to the restoring force of the walls of the squeezed vessel as explained hereinabove. This construction exhibits another benefit in that the patient himself can regulate to a desired level the rate of ultrafiltration in the artificial kidney by squeezing the artificial bladder 3 to smaller or greater extent, thus changing the resulting vacuum in the container. Loosening of the connection of the squeezed bladder 3 to the ureter 7 for a few seconds (or opening an additional valve of the vessel to the atmosphere) would allow the vacuum in the fully emptied vessel to be reduced to the desired value.

Concerning this second major function of the artificial bladder 3, in particular the generation of vacuum, it should be noted that the vacuum required for the ultrafiltration process depends on the permeability of the ultrafiltration membrane 18 and its total surface area. Determined by these parameters, vacuum can vary from about 600 mm Hg down to 20 mm Hg which is the water vapors pressure at room temperature.

It will be understood that each of the elements described above, or two or more together, may also find a useful application in other types of constructions differing from the types described above.

While the invention has been illustrated and described as embodied in an artificial kidney, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

I claim:

1. An artificial kidney system, comprising an artificial kidney forming container having an inlet blood port connectable with a patient's artery and an outlet blood port connectable with a patient's vein so that blood from the patient's artery can flow through said inlet port into said container, then through an inner space of said container and then through said outlet blood port into the patient's vein, said inner space of said container being filled with an adsorbent for removing harmful and toxic compounds from a stream of blood flowing in said inner space from said inlet blood port to said outlet blood port, said container being provided with a separate chamber formed inside said inner space and limited by a semi-permeable polymeric ultrafiltration-type membrane which allows water and dissolved small molecules to be transported from blood into said chamber; suction means connected with said separate chamber so that the water and the dissolved small molecules are transported from blood into said separate chamber and further outside of said container under the action of suction of said suction means, said container having a urine outlet communicated with said separate chamber; and artificial ureter forming tube means connecting said urine outlet of said container with said suction means so that urine with the water and dissolved small molecules is withdrawn from said separate chamber through said artificial ureter forming tube means, said suction means including a vacuum providing vessel, said artificial ureter tube means having one end connected with said urine outlet port and another end introduced into an interior of said vacuum vessel, said vacuum vessel being formed as an elastic vessel which is squeezable by a patient and restorable under elastic action of said vessel so as to form vacuum in its interior.

2. An artificial kidney as defined in claim 1, wherein said suction means include a vacuum providing vessel, said artificial ureter tube means having one end connected with said urine outlet port and another end introduced into an interior of said vacuum vessel.

3. An artificial kidney as defined in claim 2, wherein said separate chamber has a permeable wall, said semi-permeable polymeric ultrafiltration-type membrane being arranged on said permeable wall.

4. An artificial kidney as defined in claim 3, wherein said permeable wall of said separate chamber is composed of porous material.

5. An artificial kidney as defined in claim 1; and further comprising two porous filter elements, one of said filter elements being located between said inlet port and said inner space of said container and the other of said filter elements being located between said outlet port and said inner space of said container.

6. An artificial kidney as defined in claim 1; and further comprising an arterial cannula implantable in an artery of a patient and a venous cannula implantable in a vein of a patient, said arterial cannula being connectable with said blood inlet port while said venous cannula is connectable with said blood outlet port of said container, said cannulae being also connectable with one another in an inoperative position of the artificial kidney system.

7. An artificial kidney as defined in claim 1, wherein said vacuum vessel has an opening provided with a seal; and further comprising a hollow needle connectable with said another end of said artificial ureter forming tube means and piercing said seal so as to communicate said artificial ureter tube means with the interior of said vacuum vessel.

8. An artificial kidney system, comprising an artificial kidney forming container having an inlet blood port connectable with a patient's artery and an outlet blood port connectable with a patient's vein so that blood from the patient's artery can flow through said inlet port into said container, then through an inner space of said container and then through said outlet blood port into the patient's vein, said inner space of said container being filled with an adsorbent for removing harmful and toxic compounds from a stream of blood flowing in said inner space from said inlet blood port to said outlet blood port, said container being provided with a separate chamber formed inside said inner space and limited by a semi-permeable polymeric ultrafiltration-type membrane which allows water and dissolved small molecules to be transported from blood into said chamber; suction means connected with said separate chamber so that the water and the dissolved small molecules are transported from blood into said separate chamber and further outside of said container under the action of suction of said suction means, said container having a urine outlet communicated with said separate chamber; artificial ureter forming tube means connecting said urine outlet of said container with said suction means so that urine with the water and dissolved small molecules is withdrawn from said separate chamber through said artificial ureter forming tube means, said vacuum vessel having an opening provided with a seal; and a hollow needle connectable with said another end of said artificial ureter forming tube means and piercing said seal so as to communicate said artificial ureter tube means with the interior of said vacuum vessel.

9. An artificial kidney as defined in claim 8, wherein said suction means include a vacuum providing vessel, said artificial ureter tube means having one end connected with said urine outlet port and another end introduced into an interior of said vacuum vessel.

10. An artificial kidney as defined in claim 9, wherein said vacuum vessel is formed as an elastic vessel which is squeezable by a patient and restorable under elastic action of said vessel so as to form vacuum in its interior.

11. An artificial kidney as defined in claim 8, wherein said separate chamber has a permeable wall, said semi-permeable polymeric ultrafiltration-type membrane being arranged on said permeable wall.

12. An artificial kidney as defined in claim 11, wherein said permeable wall of said separate chamber is composed of porous material.

13. An artificial kidney as defined in claim 8; and further comprising two porous filter elements, one of said filter elements being located between said inlet port and said inner space of said container and the other of said filter elements being located between said outlet port and said inner space of said container.

14. An artificial kidney as defined in claim 8; and further comprising an arterial cannula implantable in an artery of a patient and a venous cannula implantable in a vein of a patient, said arterial cannula being connectable with said blood inlet port while said venous cannula is connectable with said blood outlet port of said container, said cannulae being also connectable with one another in an inoperative position of the artificial kidney system.

* * * * *